United States Patent [19]
Meglasson

[11] Patent Number: 6,008,253
[45] Date of Patent: Dec. 28, 1999

[54] USE OF 3-GUANIDINOPROPIONIC ACID TO INCREASE ENDURANCE, STAMINA AND EXERCISE CAPACITY IN A MAMMAL

[75] Inventor: Martin Durham Meglasson, Kalamazoo, Mich.

[73] Assignee: The Upjohn Company, Kalamazoo, Mich.

[21] Appl. No.: 07/751,239

[22] Filed: Aug. 26, 1991

Related U.S. Application Data

[63] Continuation-in-part of application No. PCT/US91/01109, Feb. 27, 1991, abandoned.

[51] Int. Cl.⁶ .................................................. A61K 31/195
[52] U.S. Cl. ............................................................ 514/565
[58] Field of Search ............................................. 514/565

[56] References Cited

U.S. PATENT DOCUMENTS 3,843,798  10/1974  Cook et al. ............................. 424/319

FOREIGN PATENT DOCUMENTS

| 1195199 | of 1966 | United Kingdom | ........... A61K 17/62 |
| 1195200 | of 1968 | United Kingdom | ........... A61K 27/00 |
| 1552179 | of 1976 | United Kingdom | ........... A61K 31/13 |
| WO 91/12800 | 9/1991 | WIPO . | |

OTHER PUBLICATIONS

Moerland et al. An. J Physiol 257(Cell Physiol 26): C810–816 1989.

RP Shields, et al., "Skeletal Muscle Function and Structure after Depletion of Creatine", Lab. Invest. 33: 151–158, 1975.

*Primary Examiner*—Kevin E. Weddington
*Attorney, Agent, or Firm*—Martha A. Gammill

[57] ABSTRACT

The present invention provides a new food product and use for a known compound. More particularly, the present invention provides a new food product containing 3-guanidinopropionic acid and a method of using 3-guanidinopropionic acid to increase endurance, stamina and exercise capacity.

6 Claims, 1 Drawing Sheet

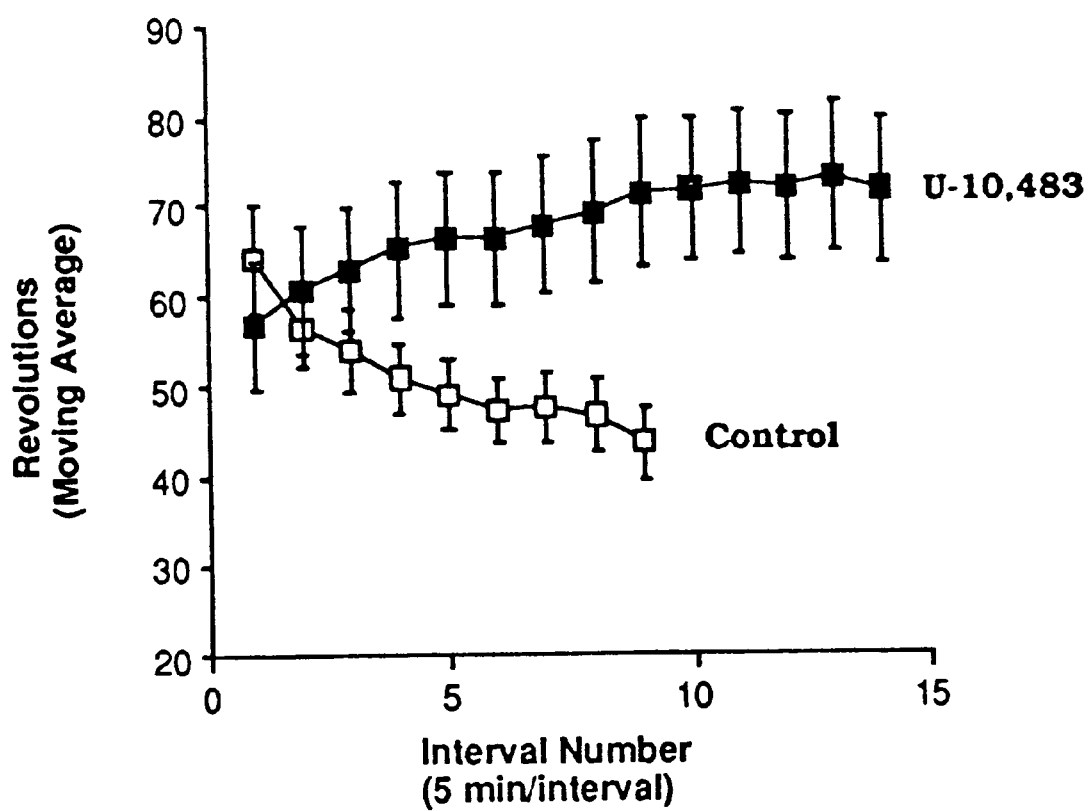

USE OF 3-GUANIDINOPROPIONIC ACID TO INCREASE ENDURANCE, STAMINA AND EXERCISE CAPACITY IN A MAMMAL

CROSS REFERENCE TO RELATED APPLICATIONS

The present invention is a continuation-in-part application of International application, PCT/US 91/01109, filed 27 Feb. 1991, which designated the U.S., now pending.

FIELD OF INVENTION

The present invention provides a new food product and use for a known compound. More particularly, the present invention provides a new food product containing 3-guanidinopropionic acid and a method of using 3-guanidinopropionic acid to increase endurance, stamina and exercise capacity.

BACKGROUND

There are several metabolic disorders of human and animal metabolism, e.g., hyperglycemia, impaired glucose tolerance, hyperinsulinemia and insulin insensitivity, hyperamylinemia, excess adiposity, and hyperlipidemia. Some or all of the above disorders may occur in the following disease states: non-insulin dependent diabetes mellitus (NIDDM), obesity, hypertension and atherosclerosis.

Hyperglycemia is a condition where the blood glucose level is above the normal level in the fasting state, following ingestion of a meal, or during a provocative diagnostic procedure, e.g., a glucose tolerance test. It can occur in NIDDM as well as obesity. Hyperglycemia can occur without a diagnosis of NIDDM. This condition is called impaired glucose tolerance or prediabetes. Impaired glucose tolerance occurs when the rate of metabolic clearance of glucose from the blood is less than that commonly occurring in the general population after a standard dose of glucose has been orally or parentally administered. It can occur in NIDDM as well as obesity, pre-diabetes and gestational diabetes.

Hyperinsulinemia is defined as having a blood insulin level that is above normal level in the fasting state, following ingestion of a meal or during a provocative diagnostic procedure. It can be seen in NIDDM or obesity and can be associated with or causal in hypertension or atherosclerosis. Hyperinsulinemia can occur without a diagnosis of diabetes. It may occur prior to the onset of NIDDM. Insulin insensitivity, also called insulin resistance, occurs when the insulin-dependent glucose clearance rate is less than that commonly occurring in the general population during diagnostic procedures such as a hyperinsulinemic clamp [See, e.g., DeFronzo, R. A. et al., Am. J. Physiol. 232:E214–E233, (1979)] or a minimal model test. See, e.g., Bergman, R. N. et al., J. Clin. Invest. 68:1456–1467 (1981). Insulin insensitivity is considered also to occur when the blood glucose concentration is higher than that commonly occurring in the general population after intravenous administration of insulin (insulin tolerance test) or when the ratio of serum insulin-to-glucose concentrate is higher than that commonly occurring in the general population after a 10–16 hour fast. Insulin insensitivity may be found in NIDDM or obesity and can also be associated with or causal to hypertension or atherosclerosis.

Hyperamylinemia is defined as having an abnormally high blood amylin level. Amylin is also known as diabetes associated peptide (DAP) and insulinoma associated polypeptide (IAP). Hyperamylinemia can be seen in NIDDM or obesity.

Excess adiposity can be seen in NIDDM associated with obesity as well as obesity without NIDDM. It is defined as a higher fat body mass-to-lean body mass ratio than the commonly occurring in the general population as measured by whole body specific gravity or other generally accepted means.

Hyperlipidemia is defined as having an abnormal level of lipids in the blood. Hyperlipidemia exists when the serum concentration of total cholesterol or total triglycerides or the serum concentration of LDL-cholesterol/HDL-cholesterol is higher than that commonly occurring in the general population. It can be seen in NIDDM or atherosclerosis.

The above disease states could be treated by either ameliorating or preventing the metabolic and biochemical disorders. In addition, humans and animals, which have not been diagnosed as having one of the above disease states but evidencing some or all of the disorders described above, could be benefitted by preventing the development of a currently recognized disease state. Therefore, a compound that is useful in the treatment of hyperglycemia, impaired glucose tolerance, hyperinsulinemia, insulin insensitivity, hyperamylinemia, excess adiposity or hyperlipidemia could also be used to treat or prevent NIDDM, obesity, hypertension or atherosclerosis.

3-Guanidinopropionic acid (3-GPA) is an endogenous metabolite found in animals and humans. See, e.g., Hiraga, Y. et al., J. Chromatography 342:269–275 (1985) and Watanabe, Y. et al., Guanidines, edited by Mori et al., Plenum, New York, pp. 49–58 (1983). The compound, which is available from Sigma Chemical Co., has been used extensively in the study of creatine metabolism [See, e.g., Walker, J. B., Adv. Enzymol. 50:177–242 (1979)] and gamma-aminobutyric acid receptor function. See, e.g., Bowery, R. et al., Br. J. Pharmacol. 50:205–218 (1974). Except as noted below, these studies do not relate to 3-GPA's utility in treating human or animal disease.

Guanidine, monoguanidine and diguanidine compounds have been shown to produce hypoglycemia. See, e.g., Watanabe, C., J. Biol. Chem. 33:253–265 (1918); Bischoff, F. et al., Guanidine structure and hypoglycemia 81:325–349 (1929). However, these compounds were observed to be toxic. In 1957, biguanide derivatives, e.g. phenformin and metformin, were used clinically as anti-diabetic agents. Some members of this class continue to be used today while others have been withdrawn from the market or banned in the United States and most Western countries. See, e.g., Schafer, G., Diabete Metabol. (Paris) 9:148–163 (1983).

Gamma-guanidinobutyramide also known as Tyformin, and the HCl salt of Tyformin, known as Augmentin, were investigated as potential anti-diabetic agents from the mid-1960's until the mid-1970's. While Augmentin produced hypoglycemia, it was reported to produce hypertension in dogs [See, e.g., Malaisse, W. et al., Horm. Metab. Res. 1:258–265 (1969)] and respiratory and circulatory collapse in rats and rabbits. See, e.g., Buckle, A. et al., Horm. Metab. Res. 3:76–81 (1971). The free acid of the amide was said to lack hypoglycemic activity [See, e.g., Beeson, M. Et al., Horm. Metab. Res. 3:188–192 (1971)].

British patent 1,153,424 discloses the use of certain esters and amides of guanidino-aliphatic acids in the treatment of diabetes mellitus where hyperuremia is present. The patent does not disclose that these compounds have an effect on hyperglycemia or any other symptom or pathological state related to diabetes. In a Canadian patent, 891509, the use of esters and amides of guanidinoaliphatic acids were disclosed for treating hyperuremia and hyperglycemia in diabetes mellitus. As noted above, the biologic activity of a guanidino alkanoic acid was known to be different and less favorable so as to be ineffective compared to its amide for treating hyperglycemia.

British patent, 1,195,199 discloses the use of guanidino alkanoic acids or their amides or esters in an insulin-containing, parenterally-administered composition for the treatment of hyperglycemia occurring in diabetes. According to this patent, the combining of a guanidino alkanoic acid, amide or ester with insulin reduces the risk of hypoglycemia as compared to insulin alone. British patent 1,195,200 discloses the use of guanidino alkanoic acids in a composition containing a guanidino alkanoic acid amide or ester derivative for the treatment of hyperglycemia occurring in diabetes. In a subsequent British patent, 1,552,179, the use of guanidino alkanoic acids, their salts, amides or esters in combination with a gluconeogensis inhibitor for treating hyperglycemic conditions was disclosed. Metformin was cited as an inhibitor of gluconeogenesis. Biological data indicated the HL 523, the preferred guanidino alkanoic acid derivative, was inactive as a single agent in six of seven experiments where blood glucose concentration was measured in alloxan diabetic mice and only weakly active in the seventh study. Most notably, British patents 1,195,199, 1,195,200 and 1,552,179 do not claim utility for guanidino alkanoic acids, as the sole active component, in compositions for treating hyperglycemic symptoms in diabetes. Among the guanidino alkanoic acids tested, several were inactive as a single agent. Thus, a variety of guanidino alkanolic acids lack significant anti-diabetic activity and combination of these compounds with an agent of known anti-diabetic activity, e.g., metformin, is necessary to show beneficial activity.

Aynsley-Green and Alberti injected rats intravenously with 3-GPA, arginine, guanidine, 4-guanidinobutyramide, and 4-guanidinobutyric acid. Arginine and 3-GPA stimulated insulin secretion transiently, but did not affect the blood glucose concentration while the other compounds stimulated insulin secretion but produced a rise in blood glucose concentration. See, e.g. Aynsley-Green A. et al., Horm. Metab. Res. 6:115–120 (1974). Blachier, et al., observed that 10 mM 3-GPA stimulated insulin secretion by isolated rat islets in vitro. See, e.g., Blachier, F. et al., Endocrinology 124:134–141 (1989). The insulin response induced by 3-GPA was 55% of that occurring when arginine was tested at the same concentration. In rats fed a diet supplemented with 10 mg/g 3-GPA for 30–60 days, the heart glycogen content was increased. See, e.g., Roberts, J. et al., Am. J. Physiol. 243:H911–H916 (1982). Similarly, skeletal muscle glycogen content was increased in rats fed chow supplemented with 10 mg/g of 3-GPA for 6–10 weeks. Mice fed a diet supplemented with 3-GPA at 20 mg/g and supplied with drinking was containing 5 mg/ml 3-GPA for 7–12 weeks had serum glucose concentrations that did not differ significantly from mice receiving unsupplemented chow and water. See, e.g., Moerland, T. et al., Am. J. Physiol. 257:C810–C816 (1989).

With respect to adiposity, it is known that in some, but not all cases [See, e.g., Shoubridge, E. et al., Biochem. J. 232:125–131 (1985)], supplementation of the diet with 10–20 mg/g 3-GPA results in decreased body weight. See, e.g., Moerland, supra and Mahanna, D. et. al., Exper. Neurol. 68:114–121 (1980). This effect has been attributed to decreased skeletal muscle mass and has not been attributed to reduced adiposity or decreased lipid storage. See, e.g., Mahanna, supra; Shields, R. et al., Lab. Invest. 33:151–158 (1975); and Otten et al.: Thyrotoxic Myopathy in Mice: Accentuation by a Creatine Transport Inhibitor. Metabolism Vol. 35, No. 6, (pages 481–484, 1986).

Patients suffering from any of the above metabolic disorders often experience lack of stamina and endurance and decreased exercise capacity. Other diseases that may result in decreased exercise ability include: diseases resulting from muscular dysfunction, such as post-poliomyelitis chronic muscle fatigue syndrome or muscular dystrophy; diseases resulting from chronic muscular weakness associated with advanced age or chronic immobilization; diseases resulting from tissue hypoxia, such as peripheral claudication; angina; myocardial infarction; and stroke.

What is needed in the art is a therapy that increases endurance, stamina and exercise capacity in patients who are performing at less that optimal levels.

INFORMATION DISCLOSURE

R. P. Shields, C. K. Whitehair, R. E. Carrow, W. W. Heusner, and W. D. Van Huss: Skeletal muscle function and structure after depletion of creatine. Lab. Invest. 33: 151–158, 1975, indicates that 3-guanidinopropionic acid results in decreased exercise tolerance in rats. In T. S. Moerland, N. G. Wolf, and M. J. Kushmerick, Administration of a creatine analogue induces isomyosin transitions in muscle. Am. J. Physiol. 257:C810–C816, 1989, 3-guanidinopropionic acid was observed to have no effect on spontaneous running activity in mice.

U.S. patent application, Ser. No. 07/486,615, filed 28 Feb. 1990, discloses a method of using 3-guanidinopropionic acid to treat or prevent excess adiposity. U.S. Patent application, Ser. No. 07/712,862, filed 10 Jun. 1991, discloses a method of using 3-guanidinopropionic acid to treat non-insulin dependent diabetes mellitus (NIDDM). The following international patent applications correspond to the above U.S. patent applications: PCT/US 91/00334, filed 22 Jan. 1991, and PCT/US 91/01109, filed 27 Feb. 1991. U.S. Pat. No. 3,843,798 discloses a method for using 3-guanidinopropionic acid to treat bacterial infections and pharmaceutical compositions useful therefor.

British patents 1,195,199and 1,195,200 and 1,552,179 refer to pharmaceutical compositions of guanidinoalkanoic acids, their esters and amides, in combination with insulin or inhibitors of hepatic gluconeogensis.

Moreland, Am. J. Physiol. 257 (Cell Physiol 26): C810–816, 1989) discloses 3-GPA as ineffective on blood glucose when administered in food to rats in high concentrations.

SUMMARY OF THE INVENTION

The present invention particularly provides:

A method of increasing endurance, stamina or exercise capacity in a mammal which comprises:

the administration to the mammal of an amount of 3-guanidinopropionic acid or a pharmaceutically acceptable salt thereof effective to increase the endurance, stamina or exercise capacity of the mammal.

The present invention also provides a food product which comprises:

a) a food; and b) 3-guanidinopropionic acid or a pharmaceutically acceptable salt thereof in an amount effective to:

1) increase the endurance, stamina or exercise capacity of a mammal in need thereof;

2) treat excess adiposity in a mammal in need thereof; or 3) treat non-insulin dependent diabetes mellitus (NIDDM) in a mammal in need thereof.

By "3-GPA" is meant 3-guanidinopropionic acid. Pharmaceutically acceptable salts of 3-guanidinopropionic acid are described in the references cited above and are well known to one of ordinary skill in the art.

By "increasing endurance, stamina or exercise capacity" is meant as increase in the ability to participate in or maintain participation in physical activity, such as exercise.

By "mammal" is meant any of a class (Mammalia) of higher vertebrates comprising man and all other animals that nourish their young with milk secreted by mammary glands and have the skin usually more or less covered with hair. Especially included in this definition are human beings, whose endurance, stamina or exercise capacity is less than optimal. Such human and non-human animals are readily diagnosed by a physician or veterinarian of ordinary skill.

By "food" or "food product" is meant a material used in the body of a mammal to sustain growth, repair, and vital processes and to furnish energy. Both solid and liquid food products are included.

By "food additive" is meant a substance that is added to a food or food product.

By "nutritional supplement" is meant a substance that supplements a mammal's nutrition, such as vitamins.

The dosage regimen for 3-guanidinopropionic acid in accord with this invention will depend on the body weight of the patient. Typically, the dose of 3-guanidinopropionic acid to be used is between 10 and 4000 mg/kg body weight daily. The preferred dose is 10–400 mg/kg/day.

3-Guanidinopropionic acid may be administered by any convenient route of administration, e.g., orally, parenterally, intranasally, intranasally, intrarectally, or topically. The oral route is preferred.

The above compositions may be administered in a sustained release formulation. By sustained release is meant a formulation in which the drug becomes biologically available to the patient at a measured rate over a prolonged period. Such compositions are well-known in the art.

3-GPA may be administered orally in conventional foodstuffs. For example, 3-GPA may be dissolved in juices, such as orange juice, preferably at a concentration of 75 mg/ml and taken by mouth. 3-GPA is adaptable to making a flavored dry mix which is constituted into a flavored beverage by simply adding water. These flavored mixes typically contain a viscosity inducing agent such as a gum or low molecular weight synthetic polymer; flavoring agents such as sucrose, aspartame or sodium saccharin; colorants; wetting agents or surfactants such as dioctyl sodium sulfosuccinate or sodium lauryl sulfate; agents to provide tartness and control acidity such as citric acid, ascorbic acid, potassium citrate or sodium citrate; flavorants such as lemon or orange; and preservative such as BHA. Similarly, 3-GPA can be used as an additive to powdered food products, including pudding and pie filling mixes, gelatin, cake mixes, powdered eggs and powdered potatoes, instant breakfast drinks, gravies and sauces (e.g., Hollandaise), prepared cereal products (e.g., oatmeal, cream of wheat, hominy grits), and drink mixes (e.g., powdered fruit punches, powdered fruit drinks). Likewise, 3-GPA can be used in prepared foods themselves; for example, it can be used as an additive in cakes, pasta products, candy, cookies, confections, yogurts, including frozen yogurt products, ice cream and ice ream products and prepared meats (hamburger, sausages and the like).

The effective amount of 3-GPA is liquid food products ranges from 10 to 400 mg/ml. Preferably the amount ranges from 70 to 300 mg/ml, with 75 mg/ml being most preferred. The effective amount of 3-GPA in solid food products ranges from 1 to 500 mg/g.

In the present invention, it has been found that 3-GPA increases exercise tolerance in normal mice (FIG. 1 and Table 1). Thus the present invention may be useful in treating muscular dysfunction, such as post-poliomyelitis chronic muscle fatigue syndrome or muscular and therefore is beneficial in treating or preventing disease states involving tissue hypoxia, e.g., peripheral claudication and exercise intolerance in diabetic humans, and angina, myocardial infarction and stroke in diabetic and normal humans.

DETAILED DESCRIPTION OF THE INVENTION

The present invention is seen more fully by the example below.

EXAMPLE 1

Effect of 3-GPA on Exercise Performance in Normal Mice

C57BL6J mice, 105–150 days of age, were obtained from Charles River Laboratories (Portage, Mich.). Mice were individually caged and maintained at 21±1° C. using a 12 h light cycle. They were allowed free access to tap water and powdered Purina 5015 mouse chew containing 20 mg/g β-GPA, resulting in a daily intake of 4 g/kg body weight, or unsupplemented chow.

Briefly, mice were placed on a standard rodent exercise wheel, 22 inches in circumference, in a pan with water to a depth of approximately ¼ inch, so that it was necessary for them to run in order to remain above the water. When a mouse ceased running the wheel was tapered by the operator to stimulate further activity. The procedure was recorded on video tape to permit data analysis.

The results of this study are presented in FIG. 1 and Table 1 below. 3-Guanidinopropionic acid increased exercise performance when administered to C57BL6J mice in the diet for one month. The total distance run, the running time, and the latency to exhaustion were increased by 3-guanidinopropionic acid.

BRIEF DESCRIPTION OF THE DRAWING

FIGURE Effect of 3-GPA on exercise performance in C57BL6J mice. Data are shown as means±S.E.M. for revolutions of the exercise wheel. Data for each 5 min interval are expressed as moving averages calculated from t=0. N=5 mice/group. 3-GPA refers to mice administered chow supplemented with 20 mg/g 3-guanidinopropionic acid for 32 days.

FORMULA CHART

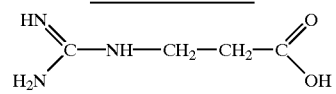

TABLE 1

Effect of 3-guanidinopropionic acid on running performance in C57BL6J mice. Compound were mixed in the chow at 20 mg/g for one month or unsupplemented chow was provided.

|  | CONTROL | 3-Guanidinopropionic acid | P-VALUE |
| --- | --- | --- | --- |
| Running rat (0–45 min) (ft/min) | 16 ± 1 | 26 ± 3 | <0.05 |
| Total distance run (0–70 min) (ft) | 719 ± 65 | 1175 ± 136 | <0.05 |
| Total distance run (0–70 min) (ft) | 719 ± 65 | 1839 ± 205 | <0.05 |
| Latency to exhaustion (min) | 45 | >70 | |

Running performance was measured in mice on an exercise wheel, 22 inches in circumference. The procedure was recorded on video tape in order to permit data analysis. Exhaustion was indicated by an abrupt decrease in running performance. In the case of 3-GPA treated mice exhaustion did not occur and the procedure was terminated by the technician after increased endurance was clearly demonstrated.

I claim:

1. A method of increasing endurance, stamina or exercise capacity in a mammal which comprises:

the administration to the mammal of an amount of 3-guanidinopropionic acid or a pharmaceutically acceptable salt thereof effective to increase the endurance, stamina or exercise capacity of the mammal.

2. The method of claim 1 wherein the mammal is a human being.

3. The method of claim 2 wherein the mode of administration is oral.

4. The method of claim 3 wherein the amount of 3-guanidinopropionic acid effective to increase the endurance, stamina or exercise capacity ranges from 10 to 4000 mg/kg/day.

5. The method of claim 4 wherein the amount of 3-guanidinopropionic acid ranges from 10 to 400 mg/kg/day.

6. The method of claim 3 wherein the 3-guanidinopropionic acid is administered as a food, a food additive or a nutritional supplement.

* * * * *